(12) United States Patent
Khouri

(10) Patent No.: US 9,402,694 B2
(45) Date of Patent: Aug. 2, 2016

(54) INTERPROXIMAL DENTAL TOOL

(76) Inventor: Louie Khouri, New York, NY (US)

(*) Notice: Subject to any disclaimer, the term of this patent is extended or adjusted under 35 U.S.C. 154(b) by 0 days.

(21) Appl. No.: 11/008,805

(22) Filed: Dec. 9, 2004

(65) Prior Publication Data
US 2006/0127845 A1 Jun. 15, 2006

(51) Int. Cl.
A61C 3/06 (2006.01)
A61C 15/04 (2006.01)

(52) U.S. Cl.
CPC .................. A61C 3/06 (2013.01); A61C 15/046 (2013.01)

(58) Field of Classification Search
CPC .................................. A61C 3/06; A61C 16/046
USPC ......... 433/39, 141–142; 606/84–85; 132/321, 132/329
See application file for complete search history.

(56) References Cited

U.S. PATENT DOCUMENTS

| 615,316 | A | | 12/1898 | Snedaker | |
|---|---|---|---|---|---|
| 1,913,598 | A | | 6/1933 | Keefe | |
| 2,288,011 | A | * | 6/1942 | Mizzy | 433/148 |
| 2,730,804 | A | * | 1/1956 | Saupe | 433/142 |
| 3,688,407 | A | | 9/1972 | Paquette | |
| 4,060,897 | A | * | 12/1977 | Greenstein | 433/144 |
| 4,109,384 | A | | 8/1978 | Dorian | |
| 4,483,676 | A | * | 11/1984 | Thierman | 433/142 |
| 4,531,530 | A | * | 7/1985 | Aiken | 132/323 |
| 4,592,729 | A | | 6/1986 | Bilciurescu | |
| 4,626,212 | A | * | 12/1986 | Mann et al. | 433/144 |
| 5,084,978 | A | | 2/1992 | McReynolds | |
| 5,090,907 | A | * | 2/1992 | Hewitt et al. | 433/144 |
| 5,476,381 | A | | 12/1995 | Dragan | |
| 5,934,291 | A | * | 8/1999 | Andrews | 132/215 |
| 6,386,873 | B1 | | 5/2002 | Blank | |
| 6,925,719 | B2 | * | 8/2005 | Callne | 30/392 |
| 2002/0119421 | A1 | * | 8/2002 | Gratz | 433/142 |
| 2003/0228554 | A1 | * | 12/2003 | Brown, Jr. | 433/142 |
| 2005/0271999 | A1 | * | 12/2005 | Fishburne, Jr. | 433/39 |
| 2006/0057540 | A1 | * | 3/2006 | Navarro | 433/166 |
| 2006/0063131 | A1 | * | 3/2006 | Kim | 433/142 |

OTHER PUBLICATIONS

The Dental Source catalog, Sullivan-Schein Dental, Mar. 2003, p. 219 Dental Catalog.
Den-Mat Catalog 2000, p. 17.
English Translation of Office Action issued by the State Intellectual Property Office for corresponding Chinese Patent Application No. 200580042167.3.

* cited by examiner

Primary Examiner — Heidi M Eide
(74) Attorney, Agent, or Firm — Harness, Dickey & Pierce, P.L.C.

(57) ABSTRACT

The present invention relates to a hand held interproximal dental tool for detaching unwanted materials from a patient's teeth and to methods of manufacturing such tools. The interproximal dental tool includes a compact, ergonomically designed housing which is gripped by a dental practitioner during use and a blade extending from and structurally supported by the housing which includes serrations for cutting or abrasive materials for sanding unwanted material.

13 Claims, 3 Drawing Sheets

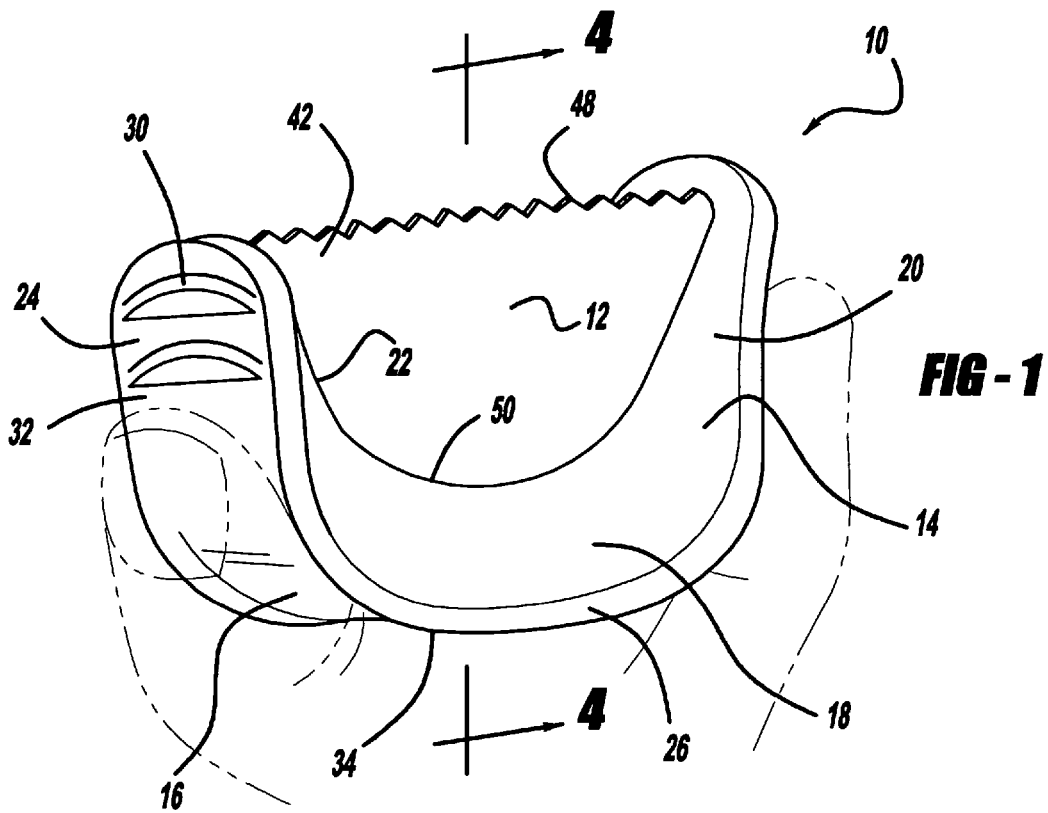
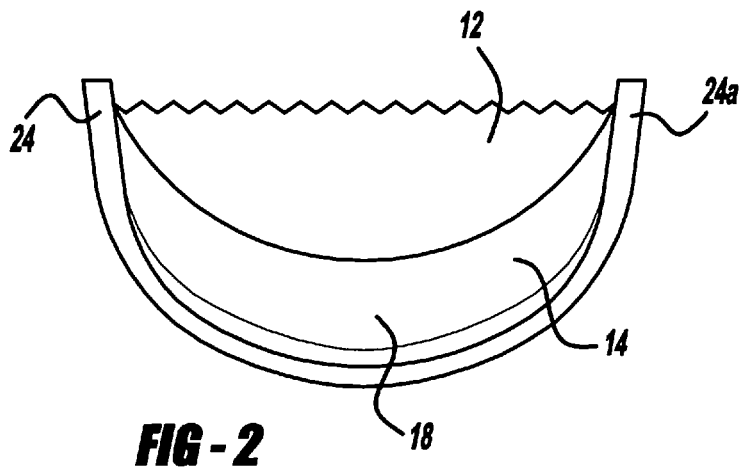
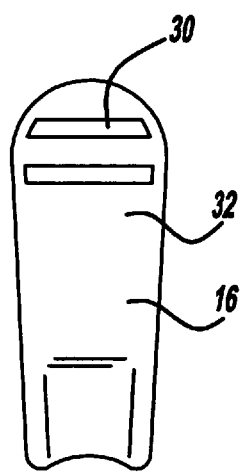

INTERPROXIMAL DENTAL TOOL

BACKGROUND OF THE INVENTION

1. Field of the Invention

The present invention relates to an interproximal dental tool, and more particularly, an interproximal dental tool for detaching unwanted material from teeth.

2. Discussion of Prior Art

Interproximal dental tools which are currently in use for detaching unwanted material by and large are ineffective, are often difficult to use and far too often lead to injuries to the patient or dental practitioner. For example, interproximal dental tools in the form of dental saws currently are elongated, flexible, thin metal strips having a serrated edge which is inserted between the teeth to remove excess or unwanted material. This type of tool is operated by gripping each end and working the tool back and forth between the teeth in order to cut away the undesired material. As such, the dental practitioner must insert at least one hand into a patient's mouth which results in discomfort to the patient. Worse yet, in the event that the tool is used on teeth posterior to the incisors, it may be required that both of the dentist's hands are at least partially inserted into the patient's mouth which is even more uncomfortable.

Another perceived problem with the prior art dental saws is that far too often injury results at least in part due to the flexible nature of the thin metal strip material. Because it is difficult to control the depth of insertion between the teeth, particularly the teeth in the posterior region of the mouth, it is not uncommon to lacerate the gum tissue with this type of prior art device. Additionally, because the serrated edge of the tool extends virtually its entire length, far too often the dental practitioner's hands are injured when handling the device.

Still another perceived problem relates to the overall effectiveness of the prior art tool. Because the tool is highly flexible to allow for the insertion between the teeth, an inherent drawback is the difficulty in generating sufficient leverage on the tool when in use to effectively remove unwanted material.

In view of the foregoing it is readily apparent there is a need in the art for an improved interproximal dental tool which is effective at removing unwanted material, easier to use, and less likely to result in injury to the patient or dental practitioner during use.

SUMMARY OF THE INVENTION

In accordance with the present invention, there is provided an interproximal dental tool for detaching material from teeth comprising:

a housing, including a body, having spaced first and second ends; and a blade fixedly attached to said housing and extending between the first and second ends, said blade including a leading portion having means for detaching material from teeth.

Examples of unwanted materials which can be detached from the teeth are materials used to repair teeth or used in cosmetic dental procedures. Such materials include by way of non-limiting example, cements, ceramics, composites, thermoplastics, and adhesives. Other unwanted materials may include calculus.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective view of an interproximal dental tool in accordance with the teachings of the present invention;

FIG. 2 is a side view of the interproximal dental tool of FIG. 1;

FIG. 3 is an end view of interproximal dental tool of FIG. 1;

DETAILED DESCRIPTION OF THE PREFERRED EMBODIMENTS

Figure 4:
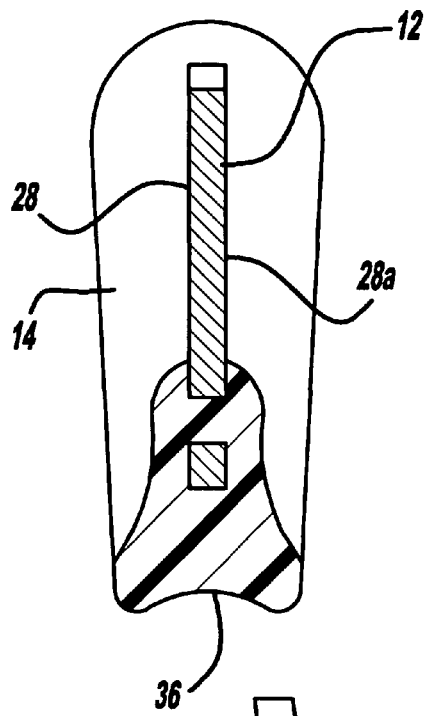
FIG. 4 is a cross sectional view taken along lines 4-4 of the interproximal dental tool of FIG. 1.
Figure 6:
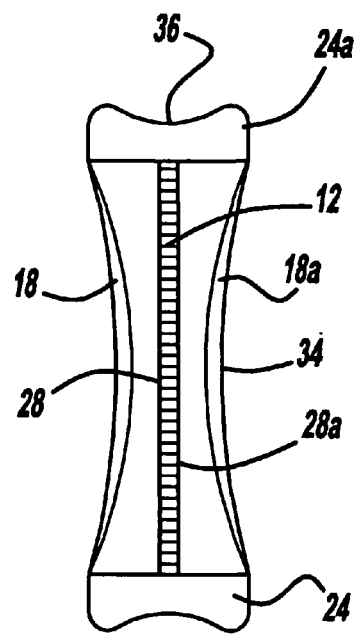
FIG. 6 is a top view of the interproximal dental tool of FIG. 1.

The following description of various embodiments is merely exemplary in nature and is in no way intended to limit the invention, its application, or uses.

Generally, the present invention describes a new and improved interproximal dental tool which is easy to use, effective and inexpensive to manufacture. Referring to FIGS. 1-6, a first embodiment of an interproximal dental tool 10 contemplated under the present invention includes as its major components, a blade 12 which is fixedly attached to a housing 14. The housing 14 which serves as a handle for gripping the tool along the outer edge 16 and/or along the respective opposing side walls 18 and 18a depending upon which teeth are being worked on, has a substantially U-shaped body 20 which results in a recess 22 extending from a first end 24 of the housing 14 to a second end 24a. Disposed within the recess 22 is blade 12 which extends from the first end 24 to the second end 24a of the housing 14. As will be described in greater detail below, the housing 14 is generally formed from a suitable injection moldable thermoplastic material which has a relatively high coefficient of friction to enhance gripping of the interproximal dental tool during use.

The housing is ergonomically sized to be conveniently used between the practitioner's index finger and thumb as shown in phantom in FIG. 1. For example, the length of the tool from the first end 24 to the second end 24a along the leading edge 42 is generally no more than about 1.25 inch. The height dimension of the dental tool as measured from the center point 34 of the housing base 26 to the leading edge 42 of the blade 12 along center line 4-4 is generally no more than about 0.75 inches. Likewise, the blade height as measured along the center line 4-4 from the terminal edge 50 of the housing to the leading edge 42 of the blade is generally no more that about 0.4 inches such that the blade can be fully inserted between the teeth. Thus, as should be appreciated, by ensuring that the blade height is no more than about 0.4 inches, the terminal edge 50 effectively serves as a stop mechanism to prevent undue penetration of the gum tissue. The width dimension at the widest point along the outer edge 16 is generally no more than about 0.5 inches. As should be appreciated by those skilled in the art, the dimensions set forth above may differ slightly for different oral care applications, provided the tool is small enough to be used between the thumb and fingers of the dental practitioner.

As shown most clearly in FIGS. 1 and 3, respectively, the outer edge 16 may include enhanced gripping means for maintaining the dental practitioner's fingers along the tool during periods of use. Thus, by way of non-limiting example horizontally aligned ribs 30 are shown that rise above the face 32 of the outer edge along at least one of the first and second ends. The side walls 18 and 18a of the housing may taper inwardly from the outer edge 16 of the housing 14 toward the blade 12 which assists in maintaining a grip when the user needs to grip the dental tool along the sides. In addition to the inward tapering, the housing material may be thinner at the center point 34 and thicker toward the ends 24 and 24a respectively such that the housing is essentially concaved along either side as depicted most clearly in FIG. 6. Likewise the outer edge 16 may be slightly concaved as indicated by reference numeral 36 in FIG. 4 to enhance gripping.

The blade 12 is generally formed from a thin, sterile metallic strip such as stainless steel. The blade as shown, includes along its length, a first edge area 40 which is embedded within the housing 14 and thus is shaped to meet the molding requirements to obtain a substantially U-shaped housing as described above. The blade 12 also includes an exposed portion including a second area 42 otherwise referred to herein as the leading edge area extending along the length of the blade opposite the first edge area and proximate to the distal portions of the first and second ends 24 and 24a of the housing. As shown in FIGS. 1-6 serrations 48 project from the leading edge area which are shaped to cut away material. The serrations 48 can vary in shape and size as is known in the art.

The average width of the blade should be no more than about 0.1 mm, and preferably no more than about 0.05 mm to effectively fit between the teeth. Widths of about 0.05 mm allow the blade to flex during use which is helpful in accessing hard to reach areas.

Figure 7:
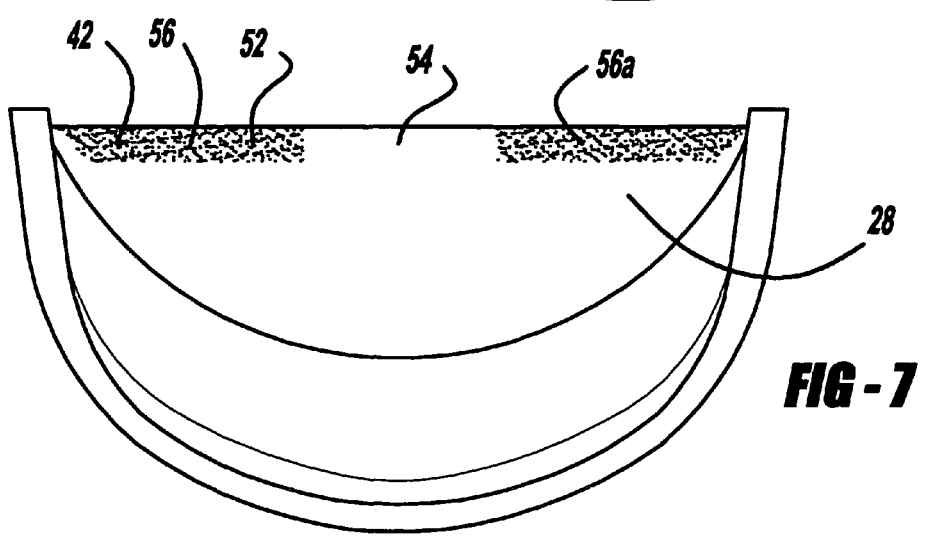
FIG. 7 is a perspective view of an alternative embodiment of an interproximal dental tool in accordance with the teachings of the present invention.

Referring to FIG. 7, an alternative embodiment is depicted. Under this embodiment, the leading edge area 42 includes a band of abrasive material 52 along at least one blade side 28 and 28a which are referenced in FIG. 6. By providing an abrasive, the dental tool of the present invention can be used when a sanding or smoothing activity is called for to detach unwanted material. As demonstrated, typically the band of abrasive will be discontinuous thereby providing an abrasive free gap 54. The abrasive free gap 54 allows for the blade to be inserted between the teeth and to avoid undesired abrasion of the teeth. The width of the abrasive band can vary according to need but typically will be less than about 0.25 inches. Additionally, the grit of the abrasive can be varied along the band such that a first section 56 has a first grit and a second section 56a has a second grit. This may allow a dental practitioner to perform both sanding (course to medium grit) and smoothing (medium to fine grit) with a single dental tool. The abrasive materials employed are considered a matter of design choice.

Figure 8:
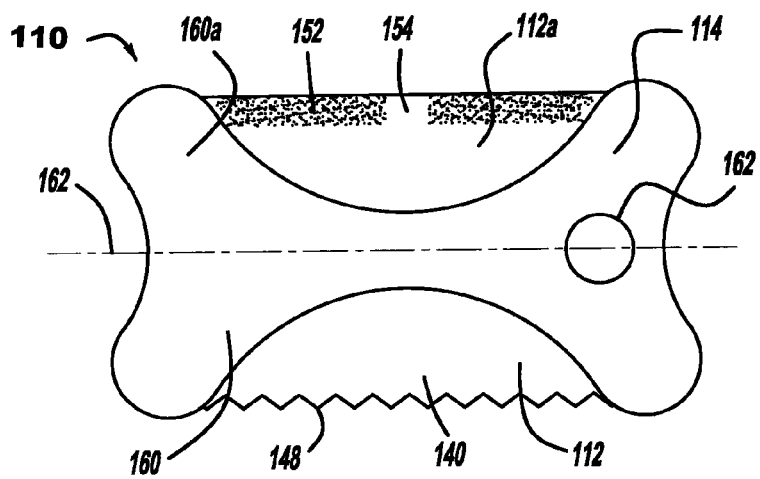
FIG. 8 is a perspective view of still another alternative embodiment of an interproximal dental tool in accordance with the teachings of the present invention.
Figure 9A:
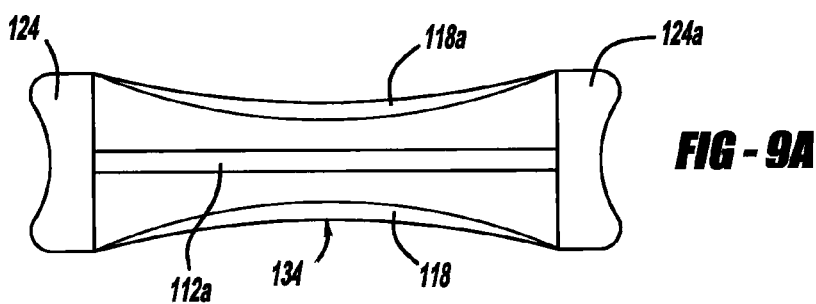
FIG. 9A is a top view of the interproximal dental tool of claim 8.
Figure 9B:
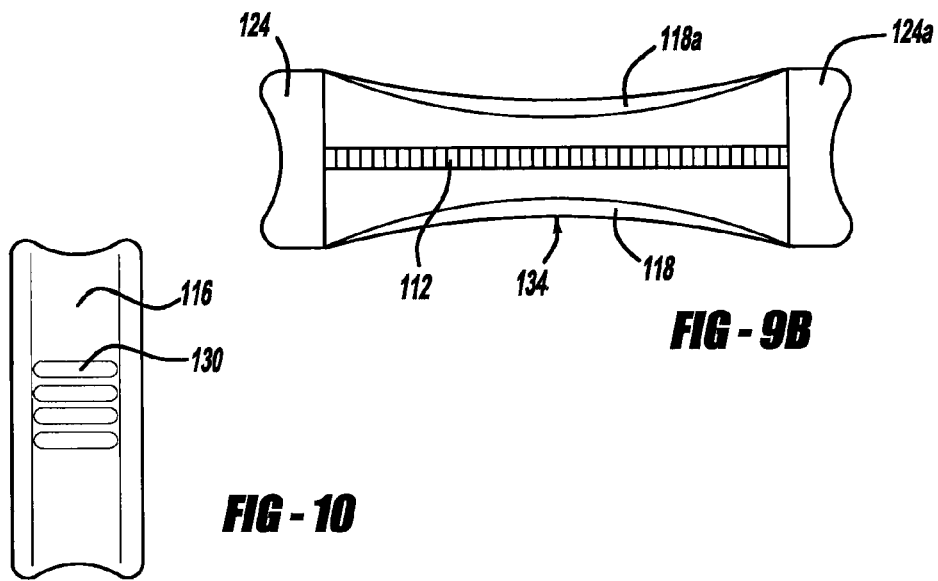
FIG. 9B is a bottom view of the interproximal dental tool of claim 8.
Figure 10:
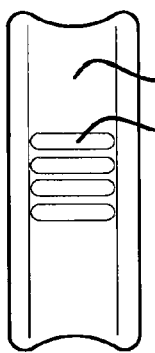
FIG. 10 is an end view of the interproximal dental tool of claim 8.

Referring to FIGS. 8-10, still another alternative embodiment is depicted. For ease in description, the reference numeral designations will be increased by 100 for previously described elements. According to this embodiment, the interproximal dental tool 110 includes two blades 112, 112a provided on opposite ends on the same tool. The body 120 of the housing 114 includes first and second opposing substantially U-shaped portions thereby resulting in an overall dog bone shape. By providing multiple blades 112, 112a the dental practitioner could optionally perform multiple tasks with a single tool. For example, as depicted in FIG. 8, the bottom half 160 of the tool 110 may include a blade 112 having serrations 148 along the edge 140 and the other half 160a of the tool may include a blade 112a having a band of abrasive material dispersed in proximity to the leading edge. As should be appreciated, such an embodiment would allow the dental practitioner the option of cutting away unwanted material with the serrated portion and optionally smoothing and sanding away unwanted material with the abrasive portion. Again, it is beneficial to include an abrasive free gap 154. Still, other combinations are anticipated with the embodiment of FIG. 8 such as both blades 112, 112a including serrations, optionally with different size and/or shaped serrations. Likewise, both blades 112, 112a could have different abrasive materials, e.g. different grits, to carry-out differing functions as described above. While reference is made to "multiple blades", it should be understood by those familiar with injection molding, the blades 112, 112a may be separate pieces or may be a single piece having two distinct blade sections.

The housing would also generally include of the features described with reference to the embodiments of FIGS. 1-7. For example, the sidewalls 118, 118a can be tapered inwardly from the dot and dash center-line 162 toward each of the perspective blades 112, 112a. Likewise, the housing material may be thinner at the center point 134 than along the ends 124, 124a as depicted in FIG. 9. The outer edge of the tool 116 may be concaved and may include ribs 130 as shown in FIG. 9.

Figure 5:
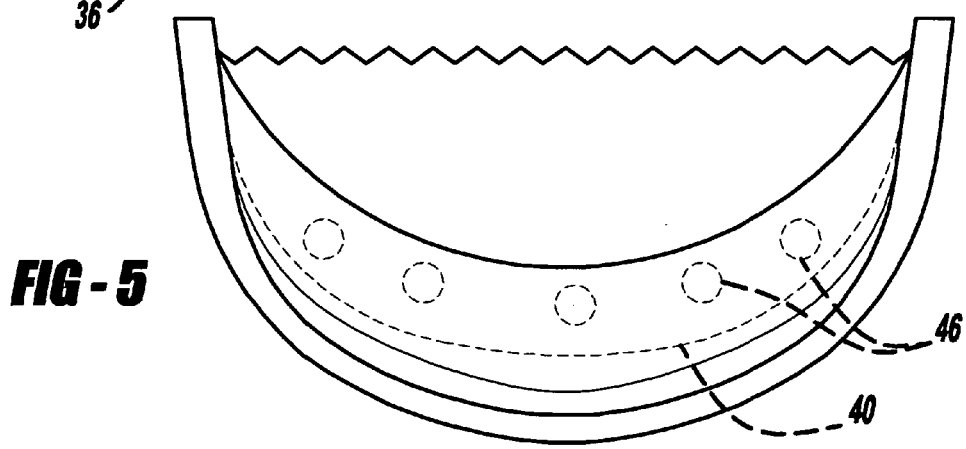
FIG. 5 is a side view of interproximal dental tool of FIG. 1 depicting a blade imbedded within the molded handle.

Regarding the manufacture of the interproximal dental tools depicted with reference to FIGS. 1-6 and 7, a preferred method involves the steps of positioning the blade 12 within an injection molding cavity and injection molding the housing 14 relative to the blade(s). Upon molding, the blade becomes fixed to the housing and projects from the housing to substantially occupy the recess 22 leaving the leading edge area and sides 28 and 28a freely exposed. Thus, the first edge area 40 of the blade 12 which is depicted with dot and dash lines is embedded in the housing. To enhance fixation of the blade 12 to the housing, the blade 12 may include a plurality of apertures 46, as shown in FIGS. 4 and 5, disposed near the first edge area 40 through which the thermoplastic material flows. Thus after injection and upon curing the thermoplastic material, an effective dynamic interproximal dental tool is achieved.

Referring to FIGS. 8-10, still another alternative embodiment is depicted. For ease in description, the reference numeral designations will be increased by 100 for previously described elements. According to this embodiment, the interproximal dental tool 110 includes two blades 112, 112a provided on opposite ends on the same tool. The body 120 of the housing 114 includes first and second opposing substantially U-shaped portions thereby resulting in an overall dog bone shape. By providing multiple blades 112, 112a the dental practitioner could optionally performing multiple tasks with a single tool. For example, as depicted in FIG. 8, the bottom half 160 of the tool 110 may include a blade 112 having serrations 148 along the edge 140 and the other half 160a of the tool may include a blade 112a having a band of abrasive material 152 dispersed in proximity to the leading edge. As should be appreciated, such an embodiment would allow the dental practitioner the option of cutting away unwanted material with the serrated portion and optionally smoothing and sanding away unwanted material with the abrasive portion. Again, it is beneficial to include an abrasive free gap 154. Still, other combinations are anticipated with the embodiment of FIG. 8 such as both blades 112, 112a including serrations, optionally with different size and/or shaped serrations. Likewise, both blades 112, 112a could have different abrasive materials, e.g. different grits, to carry-out differing functions as described above.

The description of the invention is merely exemplary in nature and, thus, variations that do not depart from the gist of the invention are intended to be within the scope of the invention.

What is claimed is:

1. An interproximal dental tool comprising:
   at least one blade; and
   a substantially U-shaped thermoplastic housing fixed to said blade, said housing including a body sized to fit substantially within a patient's mouth, having spaced apart first and second ends, a terminal edge extending between said first and second ends adjacent to the at least one blade, an outer edge which is thicker than the terminal edge and opposing side walls which extend from the outer edge to the terminal edge and include a concaved portion;
   whereby said at least one blade includes a first edge area extending along the length of said at least one blade which is permanently fixed within said substantially U-shaped housing and an exposed portion extending from the terminal edge and between the first and second ends, said exposed portion including at least one of serrations or abrasive material for detaching unwanted dental material from teeth, wherein said at least one blade is designed for use within an interproximal space between teeth, and said terminal edge of the substantially U-shaped housing provides a stop which upon complete insertion between the teeth limits insertion of the at least one blade between the teeth such that said at least one blade cannot substantially penetrate the gum line during use.

2. The interproximal dental tool of claim 1, wherein said first and second ends of said substantially U-shaped housing define end grip portions that are angled so as to diverge away from one another.

3. The interproximal dental tool of claim 1 wherein said first and second ends of the substantially U-shaped housing each include outwardly projecting grip features for enhanced gripping along said first and second ends.

4. The interproximal dental tool of claim 1, wherein the outer edge of the substantially U-shaped thermoplastic housing is at least partially concaved.

5. The interproximal dental tool of claim 1, wherein the housing is wider along said first and second ends than at an intermediate portion occurring between the first and second ends, whereby said housing is substantially concaved at the junction of the outer edge and the side walls.

6. The interproximal dental tool of claim 1, wherein the thermoplastic housing includes a hole for receiving a tether.

7. A method of manufacturing an interproximal dental tool comprising:
   a. positioning at least one blade including a first edge area along the length thereof and means for detaching unwanted material from teeth within an injection molding cavity; and
   b. injecting thermoplastic material into the molding cavity such that a substantially U-shaped housing body sized to fit substantially within a patient's mouth having an outer edge, first and second side walls extending from said outer edge to a terminal edge said side walls including a concaved portion, and spaced apart first and second ends which define at least one recess into which the at least one blade projects, wherein said terminal edge extending between said first and second ends is formed around the blade embedding a substantial portion of a blade along substantially the entire first edge area and leaving the means for detaching unwanted material from teeth freely exposed whereby said terminal edge of the housing provides a stop which upon complete insertion between the teeth, limits insertion of the at least one blade between the teeth such that said at least one blade cannot substantially penetrate the gum line.

8. The method of claim 7 wherein the portion of the blade which is embedded in the housing includes a plurality of apertures through which said thermoplastic material penetrates to enhance fixation of the blade.

9. The method of claim 7 wherein said first and second ends of said substantially U-shaped housing each include outwardly projecting grip features for enhanced gripping along said first and second ends.

10. The method of claim 7, wherein the outer edge of the substantially U-shaped thermoplastic housing is at least partially concaved.

11. The method of claim 7, wherein the housing is wider along said first and second ends than at an intermediate portion occurring between the first and second ends, whereby said housing is substantially concaved at the junction of the outer edge and the side walls.

12. The method of claim 7, wherein the thermoplastic housing includes a hole for receiving a tether.

13. The method of claim 7, wherein said first and second ends of said substantially U-shaped housing define end grip portions that are angled so as to diverge away from one another.

* * * * *